US012076182B1

(12) United States Patent
Gopinathan et al.

(10) Patent No.: US 12,076,182 B1
(45) Date of Patent: Sep. 3, 2024

(54) CHEST PATCH FOR MEASURING DISPLACEMENT OF VENTRICULAR WALLS OF SUBJECT'S HEART (71) Applicant: Analog Devices, Inc., Wilmington, MA (US)

(72) Inventors: Venugopal Gopinathan, Boston, MA (US); Tony J. Akl, Bedford, MA (US)

(73) Assignee: Analog Devices, Inc., Wilmington, MA (US)

( * ) Notice: Subject to any disclaimer, the term of this patent is extended or adjusted under 35 U.S.C. 154(b) by 78 days.

(21) Appl. No.: 17/102,162

(22) Filed: Nov. 23, 2020

Related U.S. Application Data (60) Provisional application No. 62/940,241, filed on Nov. 25, 2019.

(51) Int. Cl.
*A61B 8/08* (2006.01)
*A61B 8/00* (2006.01)

(52) U.S. Cl.
CPC .......... *A61B 8/0883* (2013.01); *A61B 8/4236* (2013.01); *A61B 8/5207* (2013.01)

(58) Field of Classification Search
CPC .... A61B 8/0883; A61B 8/4236; A61B 8/5207
See application file for complete search history.

(56) References Cited

U.S. PATENT DOCUMENTS

| | | | | | |
|---|---|---|---|---|---|
| 4,878,500 | A | * | 11/1989 | Ophir | A61B 8/00 |
| | | | | | 73/602 |
| 5,178,147 | A | * | 1/1993 | Ophir | A61B 5/0051 |
| | | | | | 600/437 |
| 5,195,521 | A | * | 3/1993 | Melton, Jr. | G01S 7/52033 |
| | | | | | 600/456 |
| 5,465,721 | A | * | 11/1995 | Kishimoto | G01S 7/52073 |
| | | | | | 600/443 |

(Continued)

FOREIGN PATENT DOCUMENTS

| | | | | |
|---|---|---|---|---|
| EP | 785746 B1 | * | 2/2004 | ......... A61B 5/02125 |
| WO | WO-200112068 A1 | * | 2/2001 | ............... A61B 8/08 |

OTHER PUBLICATIONS

Tian et al., "Association of resting heart rate and its change with incident cardiovascular events in the middle-aged and older Chinese", Scientific Reports, vol. 9, No. 6556, pp. 1-10, Apr. 2019 (Year: 2019).*

(Continued)

*Primary Examiner* — Joel Lamprecht
*Assistant Examiner* — Nyrobi Celestine
(74) *Attorney, Agent, or Firm* — ARENTFOX SCHIFF LLP (57) ABSTRACT

The present disclosure describes an apparatus for determining the condition of a subject's heart. The apparatus includes a patch adhered to a chest of the subject, the patch further including at least one ultrasound sensor for directing an ultrasound beam to the subject's heart and receiving a reflection of the beam; control circuitry for generating data (Continued)

signals based on the beam reflection indicative of a distance of the heart from the ultrasound sensor; and a processing system for receiving the data signals from the control circuitry and processing the data signals to track movement of the subject's heart over time, wherein changes in the movement correlate to the subject's heart condition.

12 Claims, 4 Drawing Sheets

(56) References Cited

U.S. PATENT DOCUMENTS

| | | | |
|---|---|---|---|
| 5,653,237 A * | 8/1997 | Uchida | A61B 8/08 600/456 |
| 8,142,358 B2 * | 3/2012 | Pedrizzetti | A61B 8/463 600/443 |
| 2003/0013958 A1 | 1/2003 | Govari | A61B 8/483 600/443 |
| 2004/0059220 A1 * | 3/2004 | Mourad | A61B 8/485 600/442 |
| 2007/0167809 A1 * | 7/2007 | Dala-Krishna | A61B 8/13 600/459 |
| 2008/0294048 A1 * | 11/2008 | Salgo | A61B 8/08 600/450 |
| 2008/0317316 A1 * | 12/2008 | Ohuchi | A61B 8/08 382/131 |
| 2011/0262018 A1 * | 10/2011 | Kumar | G06T 7/0012 382/131 |
| 2011/0319761 A1 * | 12/2011 | Abe | A61B 8/0883 600/443 |
| 2012/0065479 A1 | 3/2012 | Lahiji et al. | |
| 2012/0078097 A1 * | 3/2012 | Wang | A61B 8/0883 600/437 |
| 2012/0165674 A1 * | 6/2012 | Abe | A61B 8/5284 600/443 |
| 2012/0283567 A1 * | 11/2012 | Chono | A61B 8/5223 600/443 |
| 2013/0182935 A1 * | 7/2013 | Wang | G06V 20/69 382/133 |
| 2014/0046188 A1 * | 2/2014 | Yen | G10K 11/346 600/447 |
| 2014/0163374 A1 * | 6/2014 | Ogasawara | A61B 8/0883 600/443 |
| 2015/0148673 A1 * | 5/2015 | Yoshikawa | A61B 8/5207 600/438 |
| 2016/0004901 A1 * | 1/2016 | Wang | G06T 7/20 382/133 |
| 2016/0026213 A1 | 1/2016 | Li et al. | |
| 2017/0251930 A1 * | 9/2017 | Machida | A61B 5/0059 |
| 2018/0153506 A1 * | 6/2018 | Rodriquez | A61H 31/00 |
| 2018/0271476 A1 * | 9/2018 | Strassner | A61B 8/469 |
| 2019/0029651 A1 * | 1/2019 | Patil | A61B 8/0883 |
| 2019/0343484 A1 * | 11/2019 | Rothberg | G01S 7/52095 |
| 2020/0322454 A1 | 10/2020 | Ersson et al. | |

OTHER PUBLICATIONS

K. Inoue et al, "Ultrasonic Measurement of Left Ventricular Wall Motion in Acute Myocardial Infarction", Circulation, vol. 43, pp. 778-785, Jun. 1971 (Year: 1971).*

T. Oki et al, "Right and Left Ventricular Wall Motion Velocities as Diagnostic Indicators of Constrictive Pericarditis", American Journal of Cardiology, vol. 81, pp. 465-470, 1998 (Year: 1998).*

P. Vignon et al, "Quantitative Evaluation of Global and Regional Left Ventricular Diastolic Function With Color Kinesis", Circulation, vol. 97, No. 11, pp. 1053-1061, Mar. 1998 (Year: 1998).*

B. Lind et al, "Left ventricular isovolumic velocity and duration variables calculated from colour-coded myocardial velocity images in normal individuals", European Journal of Echocardiography, vol. 5, pp. 284-293, Nov. 2003 (Year: 2003).*

C. Storaa et al, "Tissue motion imaging of the left ventricle—quantification of myocardial strain, velocity, acceleration and displacement in a single image", European Journal of Echocardiography, vol. 5, pp. 375-385, Feb. 2004 (Year: 2004).*

L. O. Murta Jr. et al, "Automated grading of left ventricular segmental wall motion by an artificial neural network using color kinesis images", Brazilian Journal of Medical and Biological Research, vol. 39, pp. 1-7, 2006 (Year: 2006).*

T. Marwick, "Measurement of Strain and Strain Rate by Echocardiography Ready for Prime Time?", Journal of the American College of Cardiology vol. 47, No. 7, pp. 1313-1327, 2006 (Year: 2006).*

L. Stefani et al., "Two-dimensional tracking and TDI are consistent methods for evaluating myocardial longitudinal peak strain in left and right ventricle basal segments in athletes", Cardiovascular Ultrasound, vol. 5, No. 7, pp. 1-8, Feb. 2007 (Year: 2007).*

Nakashiki et al., *Usefulness of a Novel Ultrasound Transducer for Continuous Monitoring Treadmill Exercise Echocardiography to Assess Coronary Artery Disease*, Circ J 2006; 70: 6 pages.

* cited by examiner

CHEST PATCH FOR MEASURING DISPLACEMENT OF VENTRICULAR WALLS OF SUBJECT'S HEART

PRIORITY DATA

This application receives benefit from and/or claim priority to U.S. Provisional Patent Application Ser. No. 62/940,241, filed on Nov. 25, 2019, entitled, "CHEST PATCH FOR MEASURING DISPLACEMENT OF VENTRICULAR WALLS OF SUBJECT'S HEART". This U.S. Provisional Patent Application is incorporated by reference in its entirety.

FIELD OF THE DISCLOSURE

This disclosure relates generally to the field of heart ultrasound technology and, more particularly, to systems and methods for a chest patch for measuring displacement of ventricular walls of the heart of a subject.

BACKGROUND

Ultrasound waves are utilized in many different fields, often as a tool to penetrate a medium (such as a subject's skin) to measure its reflection signature. In medicine, imaging ultrasound devices are commonly used for diagnostic medical imaging of internal organs.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

A heart's ejection fraction (EF) is an indication of the heart's efficiency and is a percentage measurement of how much blood the left ventricle pumps with each contraction. The left ventricle does not empty out with each contraction; normally, the left ventricle ejects between 50% and 70% of the blood it contains. This percentage is the EF.

A heart's stroke volume (SV) is defined as the estimated amount of blood in the left ventricle when the left ventricle is completely filled (EDV) minus the estimated amount of blood remaining in the left ventricle at the end of the contraction of the left ventricle (ESV). In other words:

$$SV = EDV - ESV$$

The SV (in milliliters) is then divided by the EDV to derive the EF. In other words:

$$EF = SV/EDV$$

Figure 1A:
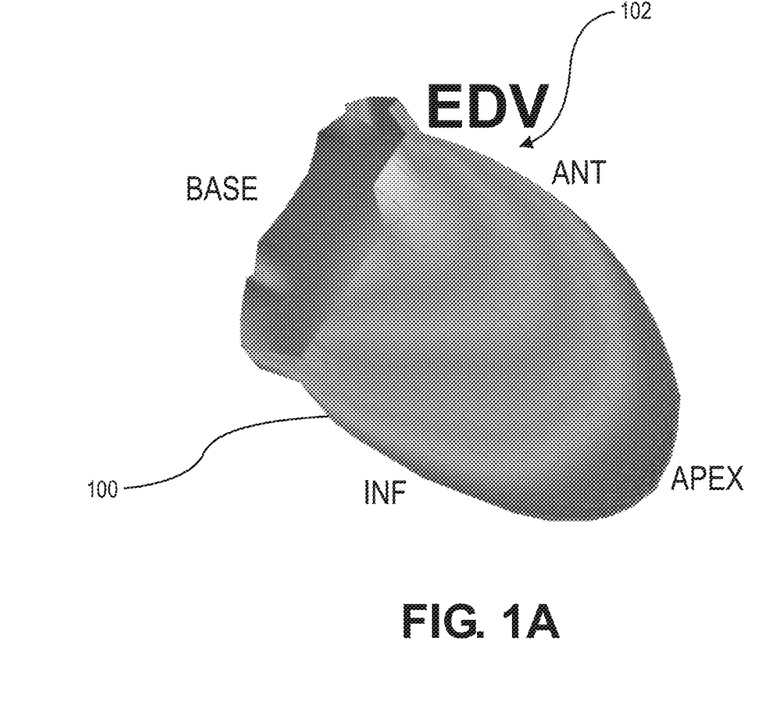
FIGS. 1A and 1B illustrate the concepts of ejection fraction (EF), stroke volume (SV), end-DIASTOLIC volume (EDV) and end-SYSTOLIC volume (ESV) in accordance with embodiments described herein.
Figure 1B:
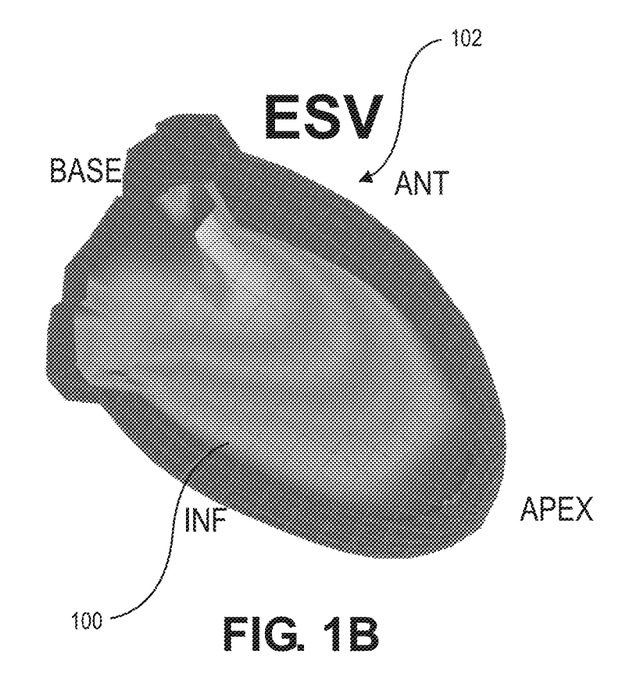

Referring to FIGS. 1A and 1B, FIG. 1A illustrates a left ventricle 100 of a heart 102 in a state of EDV, while FIG. 1B illustrates the left ventricle 100 of the heart 102 in a state of ESV.

Ventricular hypokinesis may be defined as a generalized decrease in the amplitude of the wall motion of the ventricle and correlates to low SV or EF. Ventricular hypokinesis may be caused by a number of factors, including thickening of the ventricular wall and/or an irregular area of the ventricular wall.

In accordance with features of embodiments described herein, the physical movement of the ventricular walls relative to a reference is measured (e.g., in millimeters (mm) or centimeters (cm)) and plotted over time and serves as a surrogate measurement of improvement (increased movement over time) or deterioration (decreased movement over time) of the function of the heart.

Figure 2:
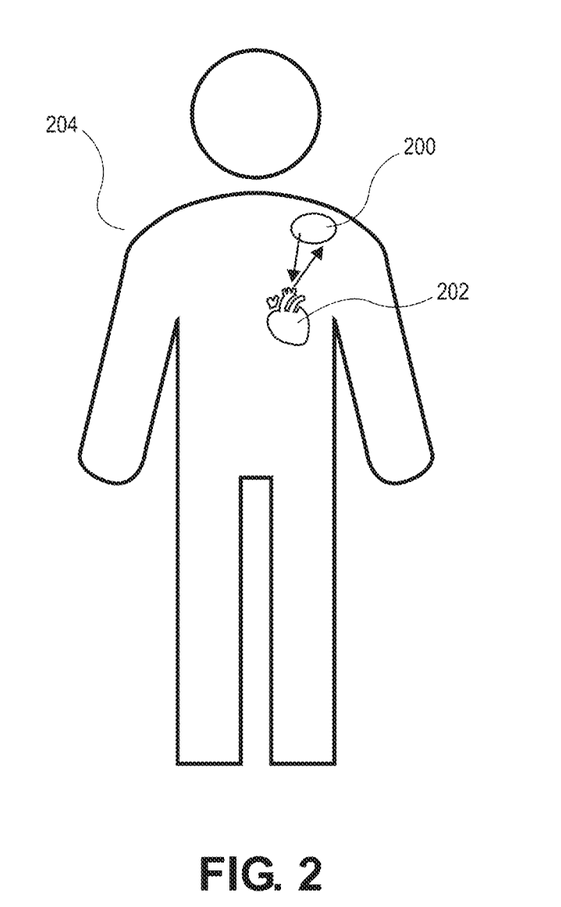
FIG. 2 illustrates a system including a patch for measuring displacement of a ventricular wall of a subject's heart using ultrasound in accordance with embodiments described herein.

As represented in FIG. 2, in one embodiment, an apparatus 200 for measuring displacement of ventricular walls of the heart 202 of a subject 204 over time includes an adhesive patch worn on the body of the subject. In certain embodiments, and as will be described in greater detail with reference to FIG. 3, the patch is affixed (e.g., using a temporary adhesive) to an area of the subject 204 proximate the heart 202 such that ultrasound beams emitted into the subject's body by one or more ultrasound sensors of an array of ultrasound sensors integrated into the patch are directed to a selected area (e.g., a ventricular wall) of the subject's heart. Reflections of the emitted beams are subsequently detected by the ultrasound sensors. Signals comprising the received reflections may be processed by control circuitry integrated into the patch and/or transmitted to a remote processing system via a communications interface of the patch. In one embodiment, signals from a certain one or more of the sensors are selected for processing. Signals, and correspondingly sensors, may be selected by virtue of the fact that both the original beam and the reflected beam are unobstructed by the subject's ribs.

In accordance with features of embodiments described herein, the selected received signals are processed (e.g., using machine learning techniques) to determine movement of the subject's heart to determine movement of the ventricular wall. In certain embodiments, only a few heartbeat cycles (comprising a measurement session) are needed to generate the signals necessary to determine movement of the ventricular wall. This measurement session process may be repeated daily, with movement plotted over time thereby enabling a determination to be made as to whether the subject's heart is moving more or less over a given time period, thereby indicating improvement (more movement over time) or deterioration (less movement over time) of the subject's heart function.

In certain embodiments, the ultrasound beams are directed to an apex of the heart. It will be noted that the axis, or other area of the heart to which the ultrasound beams are directed, may move and/or become obstructed (e.g., by one or more ribs) over time, so a mechanism should be provided in the algorithm used to process the signals derived from the beams which signal(s) to use in determining a location and movement of the heart. The algorithm may be implemented using machine learning and/or artificial intelligence techniques. In certain embodiments, multiple ultrasound sensors are provided, with the best signal (or combination of signals) being used to determine heart movement during a given measurement session. Beam steering may be used to direct a pencil thin beam or divergent beam to the same location of the heart to measure distance of movement. The signals may be synchronized to an ECG ensure accuracy of the measurement (e.g., determine where in the heartbeat cycle the ultrasound measurement was taken). Additionally, in some embodiments, radiation other than ultrasound, such as radio frequencies above 60 Ghz, may be used to penetrate the body and provide appropriate distance measurement resolution. In certain embodiments, some form of acoustic coupling mechanism (e.g., an adhesive gel) is provided on the side of the patch that adheres to the subject's skin. Additionally, a power source (e.g., a battery) may be provided within the patch for powering the sensors and other circuitry disposed on/within the patch. The power source may be implemented using any type of power source suitable for applications described herein and may be, for example, rechargeable, replaceable, or operable by a direct connection or power scavenging.

Figure 3:
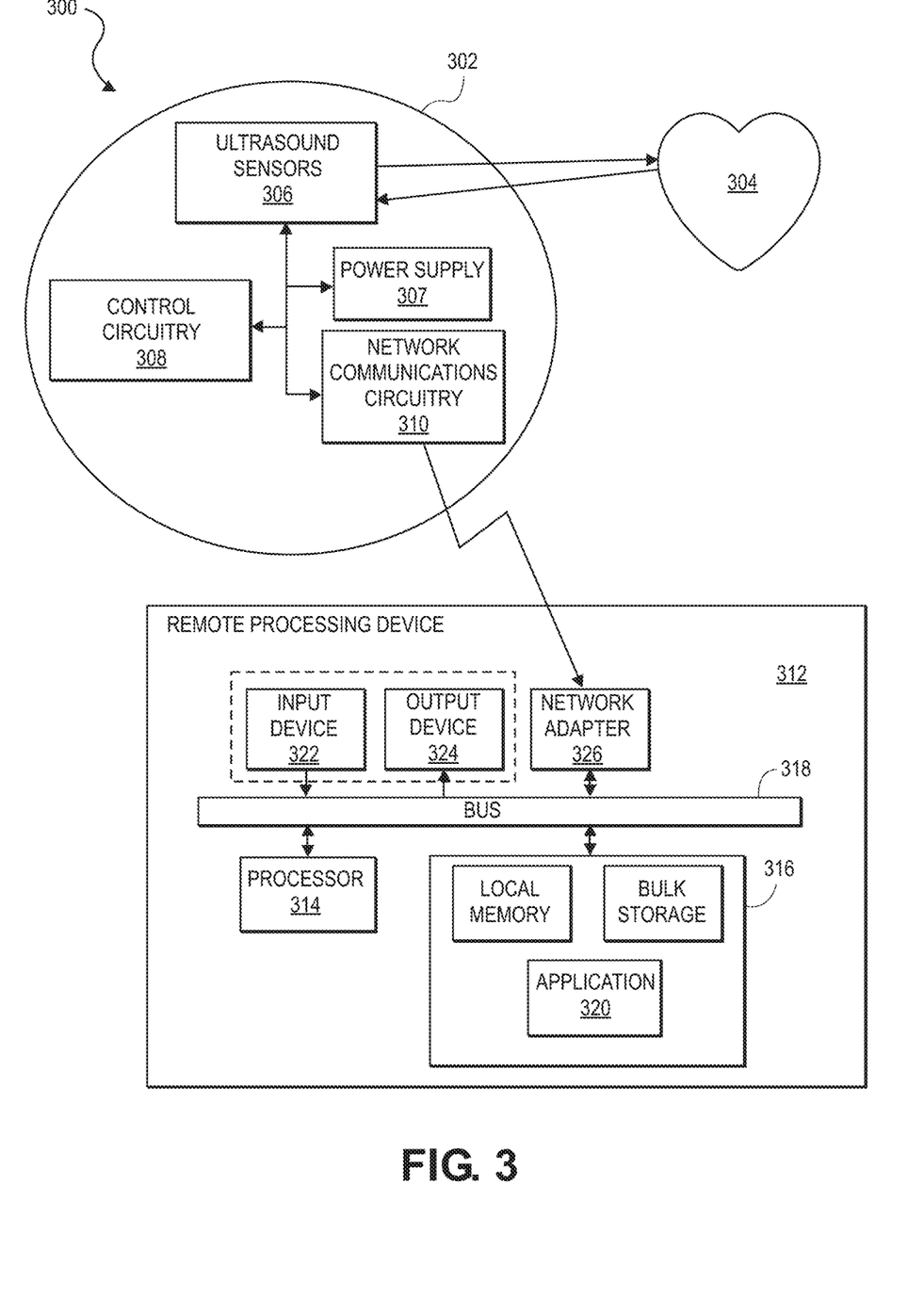
FIG. 3 is a more detailed illustration of a system including a patch for measuring displacement of a ventricular wall of a subject's heart using ultrasound in accordance with embodiments described herein.

FIG. 3 is a block diagram of a system 300 including a chest patch 302 for measuring displacement of a ventricular wall of a subject's heart 304 using ultrasound in accordance with features of embodiments described herein. As shown in FIG. 3, the patch 302 may include various devices and circuitry including one or more ultrasound sensors 306, which may be an array of ultrasound sensors comprising ultrasound transducer elements for emitting ultrasound beams through a subject's skin and toward a ventricular wall of the subject's heart 304 and for receiving reflections from the emitted beams. The patch 302 may further include a power source 307 as well as control circuitry 308 that includes a transmission system coupled to the ultrasound sensors 306 for providing signal information for transmission into the body via ultrasound beams emitted by the ultrasound sensors 306 and a receiver system coupled to the ultrasound sensors 306 for receiving ultrasound signal information reflected from the body.

The patch 302 may further include a communications interface (and appropriate circuitry) 310 for enabling external control by and/or communication with a remote processing system 312. The remote processing system 312 may include at least one processor 314, e.g. a hardware processor, coupled to memory elements 316 through a system bus 318. As such, the remote processing system may store program code 320 within memory elements 316. Further, the processor 314 may execute the program code 320 accessed from the memory elements 316 via system bus 318. In one aspect, the remote processing system 312 may be implemented as a computer that is suitable for storing and/or executing program code. It should be appreciated, however, that the remote processing system may be implemented in the form of any system including a processor and a memory that is capable of performing the functions described within this disclosure.

In some embodiments, the processor 314 can execute software or an algorithm to perform the activities as discussed in this specification, in particular activities related to a system including a patch for measuring displacement of a ventricular wall of a subject's heart using ultrasound in accordance with embodiments described herein. The processor may include any combination of hardware, software, or firmware providing programmable logic, including by way of non-limiting example a microprocessor, a DSP, a field-programmable gate array (FPGA), a programmable logic array (PLA), an integrated circuit (IC), an application specific IC (ASIC), or a virtual machine processor. The processor may be communicatively coupled to the memory element, for example in a direct-memory access (DMA) configuration, so that the processor may read from or write to the memory elements.

In general, the memory elements 316 may include any suitable volatile or non-volatile memory technology, including double data rate (DDR) random access memory (RAM), synchronous RAM (SRAM), dynamic RAM (DRAM), flash, read-only memory (ROM), optical media, virtual memory regions, magnetic or tape memory, or any other suitable technology. Unless specified otherwise, any of the memory elements discussed herein should be construed as being encompassed within the broad term "memory." The information being measured, processed, tracked or sent to or from any of the components of the remote processing system could be provided in any database, register, control list, cache, or storage structure, all of which can be referenced at any suitable timeframe. Any such storage options may be included within the broad term "memory" as used herein. Similarly, any of the potential processing elements, modules, and machines described herein should be construed as being encompassed within the broad term "processor." Each of the elements shown in the figures can also include suitable interfaces for receiving, transmitting, and/or otherwise communicating data or information in a network environment so that they can communicate with, e.g., the remote processing system of another one of these elements.

In certain example implementations, mechanisms for system including a patch for measuring displacement of a ventricular wall of a subject's heart using ultrasound as shown and described herein may be implemented by logic encoded in one or more tangible media, which may be inclusive of non-transitory media, e.g., embedded logic provided in an ASIC, in DSP instructions, software (potentially inclusive of object code and source code) to be executed by a processor, or other similar machine, etc. In some of these instances, memory elements, such as e.g. the memory elements 316 shown in FIG. 3, can store data or information used for the operations described herein. This includes the memory elements being able to store software, logic, code, or processor instructions that are executed to carry out the activities described herein. The processor 314 can execute any type of instructions associated with the data or information to achieve the operations detailed herein. In one example, the processors, such as e.g. the processor shown in FIG. 3, could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., an FPGA, a DSP, an erasable programmable read-only memory (EPROM), an electrically erasable programmable read-only memory (EEPROM)) or an ASIC that includes digital logic, software, code, electronic instructions, or any suitable combination thereof.

The memory elements 316 may include one or more physical memory devices such as, for example, local memory and one or more bulk storage devices. The local memory may refer to RAM or other non-persistent memory device(s) generally used during actual execution of the program code. A bulk storage device may be implemented as a hard drive or other persistent data storage device. The processing system may also include one or more cache memories (not shown) that provide temporary storage of at least some program code in order to reduce the number of times program code must be retrieved from the bulk storage device during execution.

As shown in FIG. 3, the memory elements 316 may store an application. In various embodiments, the application may be stored in the local memory, the one or more bulk storage devices, or apart from the local memory and the bulk storage devices. It should be appreciated that the remote processing system may further execute an operating system that can facilitate execution of the application. The application, being implemented in the form of executable program code, can be executed by the remote processing system, e.g., by the processor. Responsive to executing the application, the remote processing system may be configured to perform one or more operations or method steps described herein.

Input/output (I/O) devices depicted as an input device 322 and an output device 324, optionally, can be coupled to the remote processing system. Examples of input devices may include, but are not limited to, a keyboard, a pointing device such as a mouse, or the like. Examples of output devices may include, but are not limited to, a monitor or a display, speakers, or the like. In some implementations, the system may include a driver (not shown) for the output device. Input and/or output devices, may be coupled to the remote processing system either directly or through intervening I/O controllers.

In an embodiment, the input and the output devices 322, 324, may be implemented as a combined input/output device (illustrated in FIG. 3 with a dashed line surrounding the input device and the output device). An example of such a combined device is a touch sensitive display, also sometimes referred to as a "touch screen display" or simply "touch screen". In such an embodiment, input to the device may be provided by a movement of a physical object, such as e.g. a stylus or a finger of a user, on or near the touch screen display.

A network adapter 326 may also, optionally, be coupled to or integrated into the remote processing system 312 to enable it to be coupled to other systems, computer systems, remote network devices, and/or remote storage devices through intervening private or public networks including but not limited to the patch. The network adapter 326 may comprise a data receiver for receiving data that is transmitted by said systems, devices and/or networks to the remote processing system, and a data transmitter for transmitting data from the remote processing system to said systems, devices and/or networks. Modems, cable modems, and Ethernet cards are examples of different types of network adapter that may be used with the remote processing system.

It will be recognized that electronic elements of the patch 302 may also be implemented as described above with reference to respective elements of the remote processing system 312 and that the patch 302 may include additional elements, such as those included in the remote processing system 312, not shown in FIG. 3 as comprising part of the patch 301.f It will also be recognized that lung ultrasound can be used to differentiate between chronic obstructive pulmonary disease (COPD) and coronary heart failure (CHF) exacerbations. "B lines" are the ultrasound equivalent of Kerley B lines on a chest X-ray. Ultrasonographic B lines are long wide bands of hyperechoic artifact similar to beams of a flashlight that originate at the pleural line and traverse the entire ultrasound screen vertically to the bottom of the screen. Unilateral B lines can be caused by, for example, pneumonia and pulmonary contusion. In accordance with an alternative implementation and use of embodiments described herein, the patch may be used to generate ultrasound images of one or both lungs and subsequently analyze the images to determine whether unilateral B lines exist therein. A level of fluid congestion may be determined based on the number of B lines present in the ultrasound. As described above with reference to ventricular wall movement, the system described herein may be used to track a number of B lines over time to determine whether fluid congestion is increasing (indicated by the number of B lines increasing over time) or decreasing (indicated by the number of B lines decreasing over time).

Figure 4:
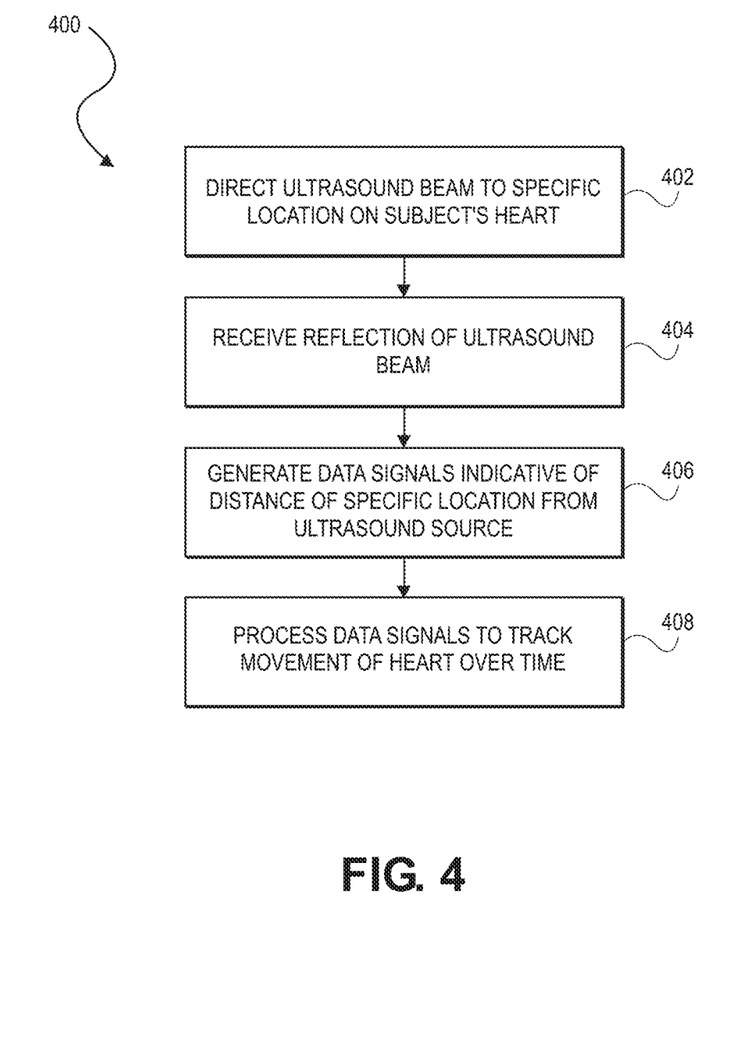
FIG. 4 is a flowchart of a method of using system including an ultrasound patch for measuring displacement of a ventricular wall of the heart of a subject in accordance with embodiments described herein.

FIG. 4 is a flowchart 400 illustrating example operation of system including an ultrasound patch for measuring displacement of a ventricular wall of the heart of a subject in accordance with embodiments described herein, such as the system 300 (FIG. 3). In an optional step, one of the sensors may be selected for use based on the subject's anatomy (e.g., a sensor that is unobstructed by one of the subject's ribs may be selected). In step 402, after an ultrasound patch has been temporarily affixed (e.g., with an appropriate adhesive) to the chest of a subject, the system directs an ultrasound beam through the subject's body to the subject's heart. In step 404, a reflection of the beam is received by the system. In step 406, data signals are generated based on the beam reflection indicative of a distance of the heart from the patch. In step 408, the data signals are processed to track movement of the subject's heart over time. Changes in the movement correlate to the subject's heart condition.

In an alternative embodiment, two reflections may be received (e.g., one reflected from the first wall of the ventricle encountered by the beam and one from the second wall of the ventricle) and processed to determine a distance between the two ventricle walls. In this embodiment, the relative movement of the ventricle walls with respect to each other may be tracked over time, with changes in movement correlating to the subject's heart condition.

Example 1 is an apparatus for determining a condition of a subject's heart, the apparatus comprising a patch adhered to a chest of the subject, the patch further comprising at least one ultrasound sensor for directing an ultrasound beam to the subject's heart and receiving a reflection of the beam; control circuitry for generating data signals based on the beam reflection indicative of a distance of the heart from the sensor; and a processing system for receiving the data signals from the control circuitry and processing the data signals to track movement of the subject's heart over time, wherein changes in the movement correlate to the subject's heart condition.

In Example 2, the apparatus of Example 1 further includes the at least one ultrasound sensor including a plurality of ultrasound sensors each directing an ultrasound beam to the subject's heart.

In Example 3, the apparatus of any of Examples 1-2 further includes the processing system further determining which at least one of the reflections comprises the most accurate image information and uses the determined at least one of the reflections in performing the tracking.

In Example 4, the apparatus of any of Examples 1-3 further includes the at least one ultrasound beam being directed to a ventricular wall of the subject's heart.

In Example 5, the apparatus of any of Examples 1-4 further includes an increase in movement over time correlating to an improvement in the condition of the subject's heart.

In Example 6, the apparatus of any of Examples 1-5 further includes a decrease in movement over time correlating to a deterioration in the condition of the subject's heart.

In Example 7, the apparatus of any of Examples 1-6 further includes the processing system synchronizing the movement data with an ECG of the subject's heart taken over an overlapping time period.

In Example 8, the apparatus of any of Examples 1-7 further includes the control circuitry including a transmission system coupled to the ultrasound sensors for providing signal information for transmission into the body via ultrasound beams emitted by the ultrasound sensor.

In Example 9, the apparatus of any of Examples 1-8 further includes the control circuitry including a receiver system coupled to the ultrasound sensors for receiving ultrasound signal information reflected from the body.

Example 10 is a method for determining a condition of a subject's heart, the method further comprising placing a patch on a chest of the subject; directing an ultrasound beam to the subject's heart and receiving a reflection of the beam; generating data signals based on the beam reflection indicative of a distance of the heart from the sensor; and receiving the data signals from the control circuitry and processing the data signals to track movement of the subject's heart over time, wherein changes in the movement correlate to the subject's heart condition.

In Example 11, the method of Example 10 may further include directing a plurality of ultrasound beams toward the subject's heart and receiving a plurality of reflections each corresponding to a respective one of the plurality of ultrasound beams.

In Example 12, the method of any of Examples 10-11 may further include determining which at least one of the reflections comprises the most accurate image information and using the determined at least one of the reflections in performing the tracking.

In Example 13, the method of any of Examples 10-12 may further include the at least one ultrasound beam being directed to a ventricular wall of the subject's heart.

In Example 14, the method of any of Examples 10-13 may further include an increase in movement over time correlating to an improvement in the condition of the subject's heart.

In Example 15, the method of any of Examples 10-14 may further include a decrease in movement over time correlating to a deterioration in the condition of the subject's heart.

In Example 16, the method of any of Examples 10-15 may further include synchronizing the movement data with an ECG of the subject's heart taken over an overlapping time period.

In Example 17, the method of any of Examples 10-16 may further include providing signal information for transmission into the body via ultrasound beams emitted by the sensors.

In Example 18, the method of any of Examples 10-17 may further include receiving ultrasound signal information reflected from the body.

Example 19 is an apparatus for determining a condition of a subject's heart, the apparatus including a patch adhered to a chest of the subject, the patch further including a plurality of ultrasound sensors each for directing an ultrasound beam to a ventricular wall of a heart of the subject and receiving a reflection of the beam; control circuitry for generating data signals based on the beam reflection indicative of a distance of the heart from the sensor; and a processing system for receiving the data signals from the control circuitry and processing the data signals to track movement of the subject's heart over time, wherein changes in the movement correlate to the subject's heart condition; wherein the processing system further determines which at least one of the reflections comprises the most accurate image information and uses the determined at least one of the reflections in performing the tracking; and wherein the processing system synchronizes the movement data with an ECG of the subject's heart taken over an overlapping time period.

In Example 20, the apparatus of Example 19 may further include the control circuitry including a transmission system coupled to the ultrasound sensors for providing signal information for transmission into the body via ultrasound beams emitted by the ultrasound sensor; and a receiver system coupled to the ultrasound sensors for receiving ultrasound signal information reflected from the body.

It should be noted that all of the specifications, dimensions, and relationships outlined herein (e.g., the number of elements, operations, steps, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, exemplary embodiments have been described with reference to particular component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system may be consolidated in any suitable manner. Along similar design alternatives, any of the illustrated components, modules, and elements of the figures may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the figures and its teachings are readily scalable and may accommodate a large number of components, as well as more complicated/sophisticated arrangements and configurations. Accordingly, the examples provided should not limit the scope or inhibit the broad teachings of the electrical circuits as potentially applied to myriad other architectures.

It should also be noted that in this Specification, references to various features (e.g., elements, structures, modules, components, steps, operations, characteristics, etc.) included in "one embodiment", "exemplary embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It should also be noted that the functions related to circuit architectures illustrate only some of the possible circuit architecture functions that may be executed by, or within, systems illustrated in the figures. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Note that all optional features of the device and system described above may also be implemented with respect to the method or process described herein and specifics in the examples may be used anywhere in one or more embodiments.

The "means for" in these instances (above) may include (but is not limited to) using any suitable component discussed herein, along with any suitable software, circuitry, hub, computer code, logic, algorithms, hardware, controller, interface, link, bus, communication pathway, etc.

Note that with the example provided above, as well as numerous other examples provided herein, interaction may be described in terms of two, three, or four network elements. However, this has been done for purposes of clarity and example only. In certain cases, it may be easier to describe one or more of the functionalities of a given set of flows by only referencing a limited number of network elements. It should be appreciated that topologies illustrated in and described with reference to the accompanying figures (and their teachings) are readily scalable and may accommodate a large number of components, as well as more complicated/sophisticated arrangements and configurations. Accordingly, the examples provided should not limit the scope or inhibit the broad teachings of the illustrated topologies as potentially applied to myriad other architectures.

It is also important to note that the steps in the preceding flow diagrams illustrate only some of the possible signaling scenarios and patterns that may be executed by, or within, communication systems shown in the figures. Some of these steps may be deleted or removed where appropriate, or these steps may be modified or changed considerably without departing from the scope of the present disclosure. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by communication systems shown in the figures in that any suitable arrangements, chronologies, configurations, and timing mechanisms may be provided without departing from the teachings of the present disclosure.

Although the present disclosure has been described in detail with reference to particular arrangements and configurations, these example configurations and arrangements may be changed significantly without departing from the scope of the present disclosure. For example, although the present disclosure has been described with reference to particular communication exchanges, embodiments described herein may be applicable to other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 142 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A method, comprising:
   placing a patch on a torso of a subject comprising an array of ultrasound sensors configured to emit ultrasound beams toward a heart of the subject;
   directing a first ultrasound beam from a first ultrasound sensor of the array of ultrasound sensors toward a select section of the heart comprising a first ventricular wall and a second ventricular wall, with the first ventricular wall being proximate to the array of sensors and spaced apart from the second ventricular wall, the first ultrasound sensor directing the first ultrasound beam to the first ventricular wall unobstructed by at least one rib of the subject;
   receiving, at the first ultrasound sensor, a first reflection of the first ultrasound beam from the first ventricular wall;
   receiving, at the first ultrasound sensor, a second reflection of the first ultrasound beam from the second ventricular wall;
   generating first data signals based on the first reflection and second data signals based on the second reflection; and
   processing the first data signals and the second data signals to track a distance between the first ventricular wall and the second ventricular wall over a time period, wherein changes in the distance between the first ventricular wall and the second ventricular wall correlate to a condition of the heart.

2. The method of claim 1, further comprising:
   directing a plurality of second ultrasound beams from the first ultrasound sensor toward the first ventricular wall;
   receiving a plurality of reflections of the plurality of second ultrasound beams, wherein a first subset of the plurality of reflections of the second ultrasound beams originates from the first ventricular wall and a second subset of the plurality of reflections of the second ultrasound beams originates from the second ventricular wall;
   directing a plurality of third ultrasound beams from a second ultrasound sensor of the array of ultrasound sensors toward the first ventricular wall;
   receiving a plurality of reflections of the plurality of third ultrasound beams, wherein a first subset of the plurality of reflections of the third ultrasound beams originates from the first ventricular wall and a second subset of the plurality of reflections of the third ultrasound beams originates from the second ventricular wall.

3. The method of claim 2, further comprising using one or more of (i) at least one select reflection of the plurality of reflections of the plurality of second ultrasound beams or (ii) at least one select reflection of the plurality of reflections of the plurality of third ultrasound beams in performing tracking of the distance between the first ventricular wall and the second ventricular wall over the time period.

4. The method of claim 1, wherein an increase in the distance between the first ventricular wall and the second ventricular wall over the time period correlates to an improvement in the condition of the heart.

5. The method of claim 1, wherein a decrease in the distance between the first ventricular wall and the second ventricular wall over the time period correlates to a deterioration in the condition of the heart.

6. The method of claim 1, further comprising synchronizing movement data indicative of the distance between the first ventricular wall and the second ventricular wall over the time period with an electrocardiogram (ECG) of the heart taken over a second time period overlapping the time period to confirm accuracy of tracking the distance between the first ventricular wall and the second ventricular wall over the time period.

7. An apparatus, comprising:
   a patch adhered to a chest of a subject, the patch comprising:
      an array of ultrasound sensors configured to emit ultrasound beams toward a heart of the subject, with a first ultrasound sensor of the array of sensors configured to:
         direct a first ultrasound beam toward a select section of the heart comprising a first ventricular wall and a second ventricular wall, with the first ventricular wall being proximate to the array of sensors and spaced apart from the second ventricular wall, the first ultrasound sensor directing the first ultrasound beam to the first ventricular wall unobstructed by at least one rib of the subject, and
         receive a first reflection of the first ultrasound beam from the first ventricular wall;
         receive a second reflection of the first ultrasound beam from the second ventricular wall;
      control circuitry to generate first data signals based on the first reflection and second data signals based on the second reflection; and
   a processing system configured to:
      receive the first data signals and the second data signals from the control circuitry and
      process the first data signals and the second data signals to track a distance between the first ventricular wall and the second ventricular wall over time, wherein changes in the distance between the first ventricular wall and the second ventricular wall correlate to a condition of the heart.

8. The apparatus of claim 7, wherein the first ultrasound sensor is further configured to:
   direct a plurality of second ultrasound beams toward the first ventricular wall; and
   receive a plurality of reflections of the plurality of second ultrasound beams, wherein a first subset of the plurality of reflections of the second ultrasound beams originates from the first ventricular wall and a second subset of the plurality of reflections of the second ultrasound beams originates from the second ventricular wall;
   the array of ultrasound sensors further comprising a second ultrasound sensor configured to:
   direct a plurality of third ultrasound beams toward the first ventricular wall; and
   receive a plurality of reflections of the plurality of third ultrasound beams, wherein a first subset of the plurality of reflections of the third ultrasound beams originates from the first ventricular wall and a second subset of the plurality of reflections of the third ultrasound beams originates from the second ventricular wall.

9. The apparatus of claim 8, wherein the processing system is configured to use one or more of (i) at least one select reflection of the plurality of reflections of the plurality of second ultrasound beams or (ii) at least one select reflection of the plurality of reflections of the plurality of third ultrasound beams in performing tracking of the distance between the first ventricular wall and the second ventricular wall over the time.

10. The apparatus of claim 7, wherein the control circuitry includes:
    a transmission system coupled to the first ultrasound sensor to provide signal information for transmission into the chest of the subject via ultrasound beams emitted by the first ultrasound sensor; and
    a receiver system coupled to the first ultrasound sensor to receive ultrasound signal information reflected from the chest of the subject.

11. The apparatus of claim 7, wherein an increase in the distance between the first ventricular wall and the second ventricular wall over the time period correlates to an improvement in the condition of the heart.

12. The apparatus of claim 7, wherein a decrease in the distance between the first ventricular wall and the second ventricular wall over the time period correlates to a deterioration in the condition of the heart.

* * * * *